United States Patent [19]

Baird

[11] Patent Number: 5,582,692
[45] Date of Patent: Dec. 10, 1996

[54] METHOD FOR THE PURIFICATION OF VITAMIN E

[75] Inventor: James L. Baird, Concord, Mass.

[73] Assignee: Artisan Industries, Inc., Waltham, Mass.

[21] Appl. No.: 320,505

[22] Filed: Oct. 7, 1994

[51] Int. Cl.⁶ .......................... B01D 3/00; C07D 311/72
[52] U.S. Cl. .................. 203/49; 203/72; 203/73; 203/78; 203/80; 203/89; 203/DIG. 16; 159/49; 549/413
[58] Field of Search ...................... 549/408, 413; 203/91, 72, 89, 73, 49, 80, DIG. 9, DIG. 16; 159/49; 202/236

[56] References Cited

U.S. PATENT DOCUMENTS

| | | | |
|---|---|---|---|
| 4,076,700 | 2/1978 | Harada et al. | 203/72 |
| 4,198,276 | 4/1980 | Johnson et al. | 203/89 |
| 4,298,622 | 11/1981 | Singh et al. | 203/91 |
| 4,613,410 | 9/1986 | Rivers, Jr. | 203/91 |
| 4,617,406 | 10/1986 | Willging | 549/413 |
| 4,810,330 | 3/1989 | Stage | 203/89 |
| 5,142,072 | 8/1992 | Stipp et al. | 554/172 |
| 5,190,618 | 3/1993 | Top et al. | 203/49 |
| 5,424,457 | 6/1995 | Sumner, Jr. | 549/408 |

FOREIGN PATENT DOCUMENTS 2135672  9/1984  United Kingdom ................. 549/413

Primary Examiner—Virginia Manoharan
Attorney, Agent, or Firm—Richard P. Crowley, Atty.

[57] ABSTRACT

A method for the separation and purification in a single pass of a heat or oxygen-sensitive liquid feed, such as a plant derived liquid feed mixture of fatty acids, tocopherol compounds and sterols, into a low boiling point purified fraction of Vitamin E tocopherol compounds and a high boiling point concentrate fraction of triglycerides, which method can be maintained in the presence of an inert gas to provide reduced degradation and increased purity of the Vitamin E fraction.

19 Claims, 1 Drawing Sheet

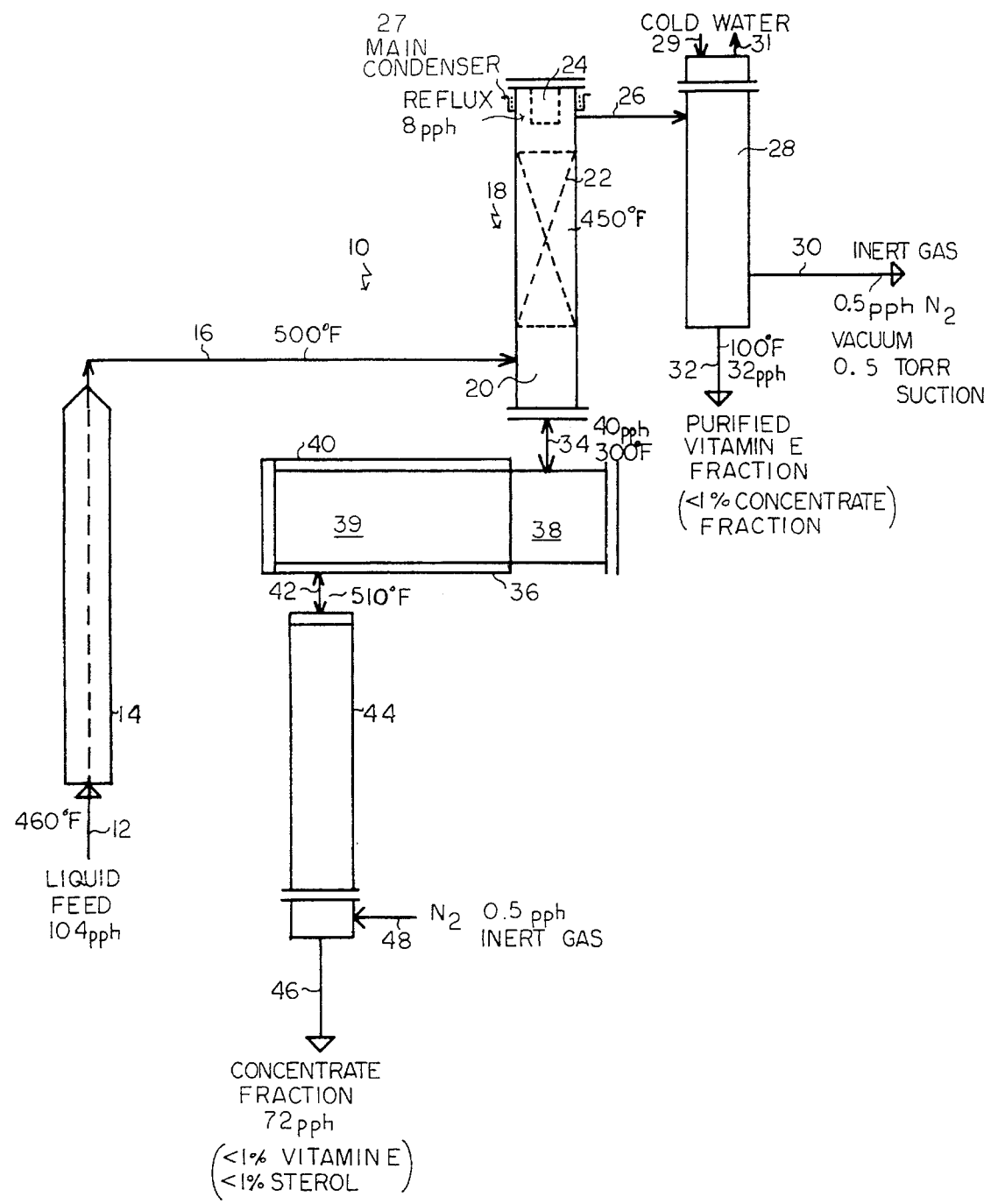

METHOD FOR THE PURIFICATION OF VITAMIN E

BACKGROUND OF THE INVENTION

Vitamin E is identified as any of a series of eight related compounds called tocopherols, with the alpha-tocopherol having the highest biological activity, and which is also associated with beta and gamma tocopherol. Tocopherol compounds are mainly present in plant materials, and generally are present in highest concentrations in plant materials such as wheat germ, corn, sunflower seed, rapeseed, soybean oils, alfalfa and lettuce. Vitamin E is a slightly viscous, pale yellow oil in the alpha-tocopherol form, and Vitamin E is believed to be required in certain human physiological processes, is subject to degradation on thermal exposure and in the presence of the atmosphere, and generally is employed as an anti-oxidant in vegetable oils and shortening, as well as pharmaceutical uses.

The tocopherol compounds constituting Vitamin E comprise a mixture of such tocopherol compounds, for example, derived from a natural product like soybean oil, the overhead fatty acid mixture from deoderization of the soybean oil, with the resulting mixture containing the alpha, beta, gamma and other tocopherols, and containing high molecular weight mixture of fatty acids and sterols, which must be separated in order to provide the Vitamin E compounds.

In view of the heat and oxygen sensitivity of the tocopherol compounds, it is customary to prepare Vitamin E from natural plant food mixtures employing molecular stills, which operate in the low micron range of pressure, which is determined from the mean free path of the molecules being processed, say, for example, from about one to fifty microns (millitorr). In some processing applications, a short path distillation procedure, such as thin film evaporation technology, may be employed, and may provide a crude mixture or fraction as desired. Similarly, whether molecular still evaporation or thin film evaporation technology is employed, it is nearly impossible to obtain high purity fractions or cuts in a single distillation pass; rather, fractions with increased purity can be obtained by multiple redistilling of the previous fraction. Thus, present separation and purification procedures provide for difficulty in operating or maintaining these high vacuum or molecular still and thin film evaporation systems, as well as high initial costs, and the difficulty of employing multiple distillations, particularly with heat-and oxygen-sensitive organic materials.

It is therefore desirable to provide for a new and improved system and method for the purification of Vitamin E, which overcomes many of the disadvantages, costs and inefficiencies associated with the prior art technology and to provide for a system and method for the purification of Vitamin E, and in particular an integral system with a single operation providing a high yield highly purified fraction of alpha-tocopherol.

SUMMARY OF THE INVENTION

The invention relates to a system and method for the purification of oxygen or heat-sensitive materials to produce a purified fraction and a concentrate fraction, and in particular relates to an integral system and single pass method for the purification of natural organic plant mixtures containing tocopherol compounds to produce a purified Vitamin E fraction.

The invention concerns a method and system for the separation of any heat or oxygen sensitive liquid feed material; such as, for example, but not limited to, plant mixtures containing tocopherol compounds like alpha, beta and gamma Vitamin E into a low boiling point purified fraction at a high yield and high efficiency, and a low boiling point concentrate fraction for subsequent recovery or processing. The method includes preheating a liquid feed to a selected temperature as desired, which, for the case of Vitamin E, is generally about 450°–500° F., to provide a preheated liquid and a preheated vapor generally in a pre-heater/evaporator, such as a tubular, plate-type or carbon block heat-type exchanger. The method includes separating the preheated liquid and preheated vapor so prepared in a vapor-liquid separating zone, typically which vapor-liquid separating zone forms an integral part of a lower portion of a distillation column to avoid pressure drop; but, which also may comprise a separate vapor-liquid separating zone or drum.

Generally, the method, in the case of Vitamin E having a temperature of 500° F. or greater, includes introducing the preheated vapor from the vapor-liquid separating zone to a lower portion of a distillation column, typically a packed distillation column, such as a column having a low pressure drop structured packing like a corrugated packing, of metal or woven wire, with the reflux column having a reflux condenser, so that the distillation column would then provide a downwardly flowing liquid reflux stream and an outlet for the withdrawal of an overhead purified vapor stream from the upper portion of the column. The reflux condenser, for the purposes of low pressure drop, preferably is located internally on the upper section of the column, or, may be a separate, outside reflux condenser which recycles a portion of the liquid back to the upper portion of the column.

The method includes introducing the preheated liquid and the liquid reflux stream from the vapor-liquid separating zone, in the lower portion of the distillation column, directly into a feed inlet in a thin film evaporator, to provide an evaporator-vapor and an evaporator liquid concentrate, with the evaporator preferably being a horizontal rotary thin film evaporator, having a thin film blade section and an aligned vapor section. The method includes introducing the evaporator vapor into the distillation column, directly into the vapor-liquid separating zone in the lower portion of the column, and the evaporator-vapor combined with the preheated vapor to provide a portion of the liquid reflux and a portion of the overhead purified vapor. The method includes withdrawing the overhead purified vapor from the upper portion of the distillation column, condensing the purified vapor stream and recovering a low boiling point purified fraction. Where the purified fraction comprises Vitamin E, for example, the purified fraction recovered includes primarily the alpha, beta and gamma tocopherol compounds and associated sterols from the plant mixture, and containing generally less than 3%, for example, 1% by weight of heavier, higher molecular weight components, and provides for a very high yield, typically of greater than 90% or greater yield of the desired Vitamin E compounds, where the feed mixture is a Vitamin E plant mixture.

In order to provide a high purified fraction, the method includes stripping by evaporation, typically with an evaporator-stripper, any lower residual amounts of the lower boiling point fractions, that is, in the tocopherol compounds in the sterols from the liquid concentrate stream derived from the thin film evaporator, to provide a residual vapor portion which is passed through the thin film evaporator into the vapor-liquid separating zone and distillation column, to help recover the residual portion of the purified fraction. The primarily tocopherols, sterols, and polyglycerides with low amounts of fatty acids, e.g., less than 5%.

| Desired Feed rate: 1.5 Tons/Day = 125 pph  Design Rate: 150 pph | | | | | | | | | |
|---|---|---|---|---|---|---|---|---|---|
| | | 1st Stage FFA Distillation | | | | | 2nd Stage Vit. E Distillation | | |
| | Feed | | Dist | | Bottoms | | Dist | | Bottoms |
| | Wt. % | pph | Wt. % | pph | wt. % | pph | wt. % | pph | wt. % | pph |
| FFA | 30 | 45 | 98 | 44 | 1 | 1 | | .1 | | |
| Vitamin E | 9 | 13.5 | 1 | .4 | 12.5 | 13.1 | | 12.6 | 1 | .5 |
| Sterols | 14 | 21 | 1 | .5 | 19.5 | 20.5 | 98.9 | 19.6 | 1 | .9 |
| Heavies | 47 | 70.5 | | | 67 | 70.5 | 1 | .3 | 98 | 70.2 |
| | | 150 | | 44.9 | | 105.1 | | 32.6 | | 71.6 | stripping by evaporation provides a heavy concentrate fraction, which heavy concentrate fraction is withdrawn from the bottom of the evaporator-stripper as a heavy concentrate fraction, which in the case of the separation of Vitamin E would constitute less than about 3%, for example 1% of the tocopherol compounds and generally less than 3%, typically 1%, of associated sterol compounds and comprise essentially all of the high boiling compounds such as the fatty acids, derived from the plant mixture. The concentrate fraction may be recovered from further processing or re-use.

Generally, in order to reduce degradation of the oxygen- or atmospheric-sensitive material, an inert gas such as nitrogen is introduced and passed through the evaporator-stripper vapor-liquid separating zone distillation column condenser.

The integral system comprises a system for the separation of a material which would normally be separated by a molecular still or by similar evaporators, into highly purified fractions, without the use of multiple passing distillation techniques, and more particularly, for a separating thermal degradable or oxygen degradable or combined degradable liquid feed material into a low boiling point purified fraction and a high boiling point concentrate fraction in a single integrated system and a single operation. The system comprises an evaporator pre-heater to preheat and evaporate a portion of the liquid feed to form a preheated liquid and a preheat vapor, and includes a vapor-liquid separation zone having an inlet for the introduction of the preheat liquid and preheat vapor and an outlet for the withdrawal of the preheat vapor received reflux liquid and an outlet for the withdrawal of the preheat liquid and an inlet for a evaporator-vapor. The inlets and outlets may comprise single integral inlets and outlets, and generally the vapor-liquid separation zone is merely a portion of the lower portion of a packed distillation column, to reduce pressure drop.

The distillate from the deoderization of the tocopherol-containing plant mixture contains fatty acids (FFA), sterols (free and esterified fatty acids), tocopherols (Vitamin E) and heavier components, particularly polyglycerides like di-and triglycerides (heavies) with molecular weights greater than about 700; e.g., 700–900. The fatty acids, like stearic acid, with lower molecular weights than the sterol, e.g., less than about 290–320, are removed prior to recovering the tocopherols. Removal of the fatty acids may be by distillation, such as, but not limited to, the similar integral inventive system as described herein except at a higher pressure or lower temperature or both. The feed mixture of the separated and purification of the Vitamin E feed thus comprises primarily tocopherols, sterols, and polyglycerides with low amounts of fatty acids, e.g., less than 5%.

The system includes a thin film evaporator, typically a generally cylindrical, rotary, thin film evaporator, for example, a Rototherm® type evaporator manufactured and sold by Artisan Industries, Inc. of Waltham, Mass. (Rototherm® is a registered trademark of Artisan Industries, Inc.). The thin film rotary evaporator has a rotary blade wiped film section and a vapor section and an inlet to introduce the preheat liquid and the reflux liquid for thin film rotary evaporation in the vapor section of the thin film evaporator, to provide an evaporator vapor, which evaporator-vapor passes through the vapor portion into the vapor-liquid separating zone in the lower section of the distillation column, and an evaporator concentrate liquid which is discharged from the outlet of the thin film evaporator directly into the upper section of the evaporator-stripper.

The employment of a wiped thin film rotary evaporator minimizes the exposure of the liquid mixture to high temperatures, e.g., over 500° F., since the processing thin film time can be quite short, such as less than 5 minutes, for example, about 1 to 3 minutes.

The use of an internal reflux condenser is desirable in systems operating at less than about 1 torr, since such reflux condensers minimize pressure drop, additional vapor piping and sources of potential air leaks.

The system includes a distillation column, such as a structured, packed bed distillation column, preferably with an integral, finger-type reflux condenser, and means to introduce the preheat vapor and evaporator vapor, generally from the lower portion of the vapor-liquid separating zone directly into the lower portion of the distillation column, and includes means to withdraw in the upper portion of the column a purified vapor fraction with means to condense the purified liquid fraction and to recover the purified liquid fraction as a purified Vitamin E fraction.

The system includes an evaporator-stripper, having an inlet to receive the liquid concentrate from the evaporator and to remove or to strip residual low boiling point purified fractions, such as the Vitamin E and sterol fractions, from the liquid concentrate to a very low or selected level, and to discharge a purified fraction as a vapor into the thin film evaporator. The evaporator stripper has an outlet to withdraw a high boiling point concentrate fraction. The stripper preferably includes a source of inert gas, which gas is introduced into the lower portion of the evaporator-stripper and circulated through the integral system and withdrawn through the purified fraction condenser.

Thus, the system comprises heating a feed mixture liquid in a preheater-evaporator which brings the feed material up to a temperature desired and evaporates from some quantity of the feed material. The vapor in the lower portion of the distillation column combines with the vapor from the thin film evaporator and goes to a distillation column, and the preheated liquid combining with the liquid from the reflux from the distillation column is introduced in a thin film rotary evaporator. The distillation column removes high boiling point components as desired to provide a highly purified fraction. The distillation column generally employs a low pressure drop packing. The thin film rotary evaporator evaporates the bulk of the preheated liquid and the reflux liquid. An evaporator-stripper is then employed at a liquid discharge outlet of the thin film rotary evaporator to strip residual desired product from the concentrate feed from the rotary evaporator. It is recognized that, naturally, other and more or less standard components such as condensers, vacuum systems, pumps and other associated components and equipment may be employed to provide for a desired complete integral system.

The system may be composed of two process stages. The first stage is designed to strip the fatty acids (FFA) from the feed stock by distillation, leaving less than 1% of the fatty acid in the bottoms and carrying over less than 1% of the Vitamin E in the distillate. The second stage of the integral system as described is designed to take the bottoms from the first stage and strip off the Vitamin E and sterols from the heavies (di- and triglycerides), leaving less that 1% Vitamin E in the bottoms and carrying over less than 1% heavies in the distillate.

Both stages may have the same equipment configuration except for the first stage degassing step, and both operate at the same vacuum of 0.5 torr. The two stages may share a common vent condenser and vacuum system. The degassing step will operate at 50 torr, and is considered a side load of the main vacuum system.

The feed is pumped to an Artisan ES2-13 Evaporator/ Stripper for degassing prior to entering a single tube rising film evaporator and is flashed into a vapor/liquid separator located between the Rototherm®"E" and a packed column. The material not evaporated in the flash evaporator is fed by gravity to the Rototherm®"E", where the remaining volatiles are further evaporated, thus leaving a small amount to be stripped in a falling-film stripper designed to remove volatiles to very low levels. The rectifying column and reflux coil located above the vapor/liquid separator are used to reduce carryover of the higher boilers in the distillate.

The integral design has the ability to process heat sensitive and viscous materials and have very low pressure drop and thus operating temperature.

The system allows the introduction of an inert gas in the evaporator-stripper step to remove further residual valuable products from the evaporator-concentrate, by further enhancing the efficiency, in recovery and purification of the purified fraction. The system that is described and disclosed allows for operation at substantially higher absolute pressures for example, one tort and above, rather than operating at low subatmospheric pressures, thus providing for a recovery of the high purity fraction product without the need for multiple distillation or other further processing steps, such as, for example, crystallization, to provide a high purity, high yield, fraction Vitamin E product. The system greatly improves the yield of the purified product from the feed mixture, the operation at higher pressures eliminates the need for installing, operating and maintaining a micron range vacuum type system, which are quite costly, all providing a significant advantage, both in installation, operating costs and yield and purity, in treating oxygen and heat-sensitive products.

The invention will be described in connection with a certain illustrated embodiment; however, it is recognized that those persons skilled in the art may make various improvements, additions, modifications, and changes to the illustrated embodiments without imparting from the spirit and scope of the invention.

BRIEF DESCRIPTION OF THE DRAWING

FIG. 1 is a schematic illustration of a system and method for the separation of liquid plant (soybean) feed mixture to provide for a high yield, high purified fraction of Vitamin E.

DESCRIPTION OF THE EMBODIMENTS

The feed mixture employed in the illustrated embodiments is a soybean oil mixture derived from deodorizing soybean oil and represents the overhead mixture of a variety of fatty acids together with tocopherol compounds and sterol. It is recognized that such mixtures or similar mixtures may vary in the amount of tocopherol and sterol compounds, and fatty acid compounds present, but typically the Vitamin E tocopherol compounds range from about 10 to 35% by weight of the feed mixture. The temperatures may vary as desired, based on the liquid feed mixture employed and the desired efficiency and purity of the fraction desired, or of the concentrate fraction.

As illustrated, the Vitamin E distillation system 10 includes a liquid feed inlet 12, connected to a preheater-evaporator 14 leading to a packed bed distillation column 18 by means of a connecting line 16. The packed bed distillation column has a vapor-liquid separation zone 20 in the lower portion, a low pressure, corrugated, packed bed 22 in the middle of the column, an internal, finger-type reflux condenser 24 and a main condenser 27 at the top portion of the column. The system also includes a condenser 28 connected by line 6 to the top portion of the distillation column 18, with the condenser 28 having a cold water inlet 29 and cold water outlet 31 and having a withdrawal outlet 30 for nitrogen gas and a recovery line 32 for the recovery of the purified Vitamin E fraction.

A thin film rotary evaporator 36 is connected to the lower portion 20 of the distillation column 18 by means of connecting line 34, said thin film evaporator having a thin film 40 with a vapor-liquid separating zone 38, a liquid zone 39, and an outlet 42 connected to an evaporator-stripper 44. The evaporator-stripper 44 has an outlet 46 at the bottom for withdrawal of the high boiling point concentrate fraction, and an inlet 48 toward the bottom for the introduction of nitrogen gas into the system.

In operation, the oxygen and heat-sensitive liquid feed material, for example, a plant inlet 12 into a preheater-evaporator 14, which preheater-evaporator preheats the liquid feed to provide a preheated liquid and a preheated vapor, which preheated vapor and preheated liquid enter into a distillation column 18 through connecting line 16. The preheated vapor and liquid enter the distillation column at the bottom, where a vapor-liquid separating zone 20 is located. At this point, the preheated vapor and liquid are separated, with the vapor rising through a packed bed structure 22 in the distillation column 18, further separating the liquid and vapor, with the purified vapor rising to the top of the distillation column 18 where a reflux condenser 24 is located, which provides a downwardly flowing reflux stream and an overhead purified vapor stream which is withdrawn from the upper portion of the column 18 through withdrawal line 26, whereupon the purified vapor stream enters a condenser 28 and condensation is provided by circulation of water through cold water inlet 29 and cold water outlet 31, and a purified Vitamin E fraction is recovered at the bottom of the condenser through recovery line 32.

The method further includes introducing the preheated liquid (separated in the vapor-liquid separating zone 20) and the residual reflux liquid from the distillation column 18, directly into a feed inlet 34 to a thin film evaporator 36, where the mixture is separated by thin film 40 evaporation to provide an evaporator-vapor, which remains in the vapor zone 38 and passes up through to the distillation column 18, and an evaporator liquid concentrate, which enters the liquid zone 39 and passes into the evaporator-stripper 44 through connecting line 42, where the heavy concentrate is further separated, with any residual vapor returning through and passing up through the system, and the heavy concentrate fraction being withdrawn from outlet 46 at the bottom of the evaporator-stripper 44.

Generally, in order to reduce degradation of the oxygen- or atmospheric-sensitive material, an inert gas such as nitrogen is introduced through inlet 48 at the bottom of the evaporator-stripper 44, and passed through the system, whereupon the nitrogen gas is recovered through withdrawal line 30 and recycled for use.

The temperatures employed in the system and method are set forth in the drawing, together with the description of the feed mixture, purified fraction and concentrate fraction separated in parts per hundred parts (pph).

This system and method for purification of heat- and oxygen-sensitive materials, such as Vitamin E containing compounds, as described and illustrated provides for increased yield of enhanced purity Vitamin E and concentrate fractions without multi-pass or repeated distillation, due to the integral distillation system employing multiple purification steps within the system. The system and method also provides for decreased degradation of the fractions produced, due to improved temperature control and the introduction of an inert gas into the system, such as nitrogen gas, to prevent deterioration of the Vitamin E compounds by oxidation and overheating. The integral system and method of the invention is less costly to initiate, operate and maintain over prior art vacuum and redistillation systems.

What is claimed is:

1. A method for the separation and purification of a heat or oxygen sensitive liquid organic feed in a single pass into a low boiling point purified fraction and a high boiling point concentrate fraction, which method comprises:

a) preheating a liquid to a selected temperature to provide a preheated feed liquid and a feed vapor;

b) separating the preheated feed liquid and said feed vapor in a vapor-liquid separating zone;

c) introducing said feed vapor into a packed distillation column with a reflux condenser to provide a downwardly flowing liquid reflux stream and an overhead purified vapor stream enriched in the low boiling point purified fraction;

d) introducing the preheated feed liquid and the liquid reflux stream from the distillation column as a liquid mixture into a thin film evaporator to provide an evaporator vapor containing an enriched low boiling point fraction and a liquid concentrate enriched in said high boiling point concentrate fraction;

e) introducing the evaporator vapor into the distillation column to provide a portion of the liquid reflux and a portion of the overhead purified vapor;

f) withdrawing the overhead purified vapor stream from the distillation column condensing the purified vapor stream and recovering a low boiling point purified fraction having less than about three percent by weight of the high boiling point concentrate fraction;

g) stripping by evaporation in an evaporator-stripper residual amounts of low boiling point fraction from the liquid concentrate from the thin film evaporator to provide a residual vapor portion of the evaporator vapor which is withdrawn from the evaporator-stripper and directly added to the evaporator/vapor and the high boiling point concentrate fraction in the thin film evaporator, and;

h) withdrawing from the evaporator-stripper the high boiling point concentrate fraction having less than about three percent by weight of the low boiling point purified fraction.

2. The method of claim 1 which includes preheating the liquid feed to a temperature of about 450°–500° F.

3. The method of claim 1 which includes employing a lower portion of the packed distillation column as the vapor-liquid separating zone.

4. The method of claim 1 wherein the liquid feed comprises a plant derived mixture containing tocopherol compounds.

5. The method of claim 4 wherein the liquid feed comprises a soybean oil derived mixture of tocopherols, sterol and fatty acids, and Vitamin E compounds are the purified fraction.

6. The method of claim 5 wherein the low boiling point purified fraction comprises Vitamin E and sterols with less than about three percent by weight of the high boiling point concentrate fraction.

7. The method of claim 1 which includes carrying out the method of steps g) through h) in the presence of an inert gas.

8. The method of claim 1 wherein step e) includes refluxing with an internal reflux element in an upper portion of the distillation column.

9. The method of claim 1 wherein the concentrate fraction has less than about three percent by weight of Vitamin E and less than about three percent by weight of sterols.

10. The method of claim 1 which includes carrying out the condensing and recovering of step f) at an absolute pressure of 0.5 torr or above.

11. The method of claim 1 which includes preheating the liquid feed in a rising film evaporator-stripper.

12. The method of claim 1 wherein the liquid feed comprises tocopherols, sterols and di and triglycerides with less than about five percent by weight of fatty acids.

13. The method of claim 1 which includes exposing the liquid mixture in the thin film evaporator to a temperature of greater than 500° F. for less than five minutes.

14. The method of claim 1 wherein the high boiling point concentrate fraction of step h) contains less than about three percent by weight of tocopherol compounds and less than about three percent by weight of sterol compounds.

15. The method of claim 1 wherein the thin film evaporator of step d) comprises a horizontal, thin film evaporator having a thin film section and a directly adjoining, aligned vapor section;

introducing the liquid mixture directly into the vapor section of the thin film evaporator; and introducing the evaporator vapor from the vapor section of the thin film evaporator directly into the lower portion of the distillation column.

16. The method of claim 1 wherein the liquid feed comprises a liquid distillate from the deodorization of a tocopherol-containing plant mixture.

17. The method of claim 1 wherein the liquid feed comprises from about 10 to 35 percent by weight of Vitamin E.

18. A method for the separation and purification in a single pass a liquid mixture feed comprising fatty acids, tocopherol compounds, di and triglycerides and sterols into a low boiling point purified Vitamin E fraction and a high boiling point concentrate fraction, which method comprises;

a) preheating the liquid feed to a selected temperature to provide a preheated feed liquid and feed vapor;

b) separating the preheated feed liquid and said feed vapor in a vapor-liquid separating zone, said zone located in a lower portion of a low pressure drop packed distillation column with an internal reflux condenser;

c) introducing said feed vapor into the lower section of the packed distillation column condenser to provide a downwardly flowing liquid reflux stream and an overheated purified vapor stream enriched in Vitamin E;

d) introducing the preheated feed liquid and the liquid reflux stream from the distillation column directly into a vapor section of a thin film rotary evaporator having a vapor section and a thin film section to provide an evaporator vapor and a liquid concentrate;

e) introducing the evaporator vapor into the lower portion of the distillation column;

f) withdrawing the overhead purified vapor from the distillation column, condensing the purified vapor and recovering a low boiling point liquid purified fraction of Vitamin E compounds having less than about three percent by weight of di and triglycerides and fatty acids;

g) stripping by evaporation in an evaporator-stripper residual amounts of low boiling, point purified fraction from the liquid concentrate from the thin film evaporator to provide a residual vapor portion of the evaporator vapor stream which is withdrawn from an upper portion of the evaporator-stripper and added to the evaporator vapor stream and a heavy high boiling point concentrate fraction; and h) withdrawing the heavy high boiling point concentrate fraction from the lower portion of the evaporator-stripper, the concentrate fraction enriched in fatty acids and di and triglycerides and having less than about three percent by weight of Vitamin E.

19. The method of claim 18 which further comprises introducing a nitrogen gas in a lower portion of the evaporator-stripper and through the thin film evaporator and distillation column and recovering the nitrogen gas and recycling the recovered nitrogen.

* * * * *

UNITED STATES PATENT AND TRADEMARK OFFICE
CERTIFICATE OF CORRECTION

PATENT NO.  : 5,582,692
DATED       : December 10, 1996
INVENTOR(S) : James L. Baird It is certified that error appears in the above-indentified patent and that said Letters Patent is hereby corrected as shown below:

```
Col. 3, lines 27-28, delete "such as the fatty acids".
Col. 5, line 57, delete "tort" and insert --torr--.
Col. 6, line 54, after "a plant" insert --mixture,
        containing tocopherol compounds like alpha,
        beta and gamma Vitamin E compounds mixed with
        high molecular weight fatty acids and sterols,
        is introduced through a liquid feed.--.
Col. 8, line 2, after "column" insert --,--.
Col. 8, line 59, after "section", delete ";" and insert
        --and which method includes:--.
```

Signed and Sealed this

Ninth Day of December, 1997

Attest:

BRUCE LEHMAN

Attesting Officer

Commissioner of Patents and Trademarks